US011966267B2

(12) United States Patent
Dory et al.

(10) Patent No.: US 11,966,267 B2
(45) Date of Patent: Apr. 23, 2024

(54) THERMO-ELECTRIC COOLING HEADSETS

(71) Applicant: Hewlett-Packard Development Company, L.P., Spring, TX (US)

(72) Inventors: Jon R. Dory, Spring, TX (US); Matthew Flach, Fort Collins, CO (US); David H. Hanes, Fort Collins, CO (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 79 days.

(21) Appl. No.: 17/628,243

(22) PCT Filed: Sep. 30, 2019

(86) PCT No.: PCT/US2019/053737
§ 371 (c)(1),
(2) Date: Jan. 19, 2022

(87) PCT Pub. No.: WO2021/066782
PCT Pub. Date: Apr. 8, 2021

(65) Prior Publication Data
US 2022/0261053 A1 Aug. 18, 2022

(51) Int. Cl.
*G06F 1/20* (2006.01)
*A61F 7/00* (2006.01)
*G06F 3/01* (2006.01)
*H04R 1/10* (2006.01)
*G02B 27/01* (2006.01)

(52) U.S. Cl.
CPC ............... *G06F 1/206* (2013.01); *A61F 7/00* (2013.01); *G06F 3/011* (2013.01); *H04R 1/1091* (2013.01); *A61F 2007/0002* (2013.01); *G02B 27/0176* (2013.01); *H04R 1/1008* (2013.01)

(58) Field of Classification Search
CPC .......... G06F 1/206; G06F 3/011; G06F 1/163; A61F 7/00; A61F 2007/0002; H04R 1/1091; H04R 1/1008; H04R 5/033; H04R 1/1083; G02B 27/0176
See application file for complete search history.

(56) References Cited

U.S. PATENT DOCUMENTS 6,000,225 A * 12/1999 Ghoshal ................. H10N 10/17
62/3.7
8,581,089 B2 11/2013 Teunissen et al.
9,414,966 B2 8/2016 Ji
(Continued)

FOREIGN PATENT DOCUMENTS

CN 208581339 U 3/2019
JP 0678386 A 3/1994
(Continued)

*Primary Examiner* — Zhipeng Wang
(74) *Attorney, Agent, or Firm* — Quarles & Brady LLP

(57) ABSTRACT

In one example in accordance with the present disclosure, a headset is described. The headset includes a sensory input device and a pad surrounding the sensory input device. The pad includes a thermo-electric cooling (TEC) device having a first side and a second side. The first side is to cool and the second side is to heat when a voltage is applied to the TEC device. The pad also includes a cooling layer in contact with the first side of the TEC device and a heat spreading layer in contact with the second side of the TEC device. The pad also includes an enclosing material enveloping the pad.

20 Claims, 7 Drawing Sheets

(56) References Cited

U.S. PATENT DOCUMENTS

| | | |
|---|---|---|
| 10,075,786 B2 | 9/2018 | Larsen |
| 10,712,791 B1* | 7/2020 | Stanley .................. G06F 1/206 |
| 2010/0107657 A1* | 5/2010 | Vistakula ........... A41D 13/0056 |
| | | 62/3.5 |
| 2015/0092972 A1 | 4/2015 | Lai et al. |
| 2017/0099539 A1* | 4/2017 | Di Censo ............... G05D 23/00 |
| 2018/0008457 A1 | 1/2018 | Smith et al. |
| 2018/0262827 A1* | 9/2018 | Vaughan ............. H04R 1/1041 |

FOREIGN PATENT DOCUMENTS

| | | |
|---|---|---|
| KR | 10-2014-0036469 A | 3/2014 |
| KR | 20160055640 A | 5/2016 |
| WO | 95/35560 A1 | 12/1995 |
| WO | 2018/048766 A1 | 3/2018 |
| WO | WO-2018-139995 A1 | 8/2018 |
| WO | WO-2018-194686 A1 | 10/2018 |
| WO | WO-2018-194689 A1 | 10/2018 |
| WO | WO-2019-151988 A1 | 8/2019 |
| WO | WO-2020-046320 A | 3/2020 |

\* cited by examiner

THERMO-ELECTRIC COOLING HEADSETS

BACKGROUND

Headsets are used with electronic devices to provide audio and/or visual input to a user. For example, a user may wear headphones that provide audio input to a user. Another example of a headset is a virtual reality headset that provides a visual display to a user. Such headsets are used in a number of scenarios including business environments for example to collaborate/communicate with individuals at different locations and can also be used for personal entertainment. For example, an audio and/or video headset can be used to engage in video games.

BRIEF DESCRIPTION OF THE DRAWINGS

The accompanying drawings illustrate various examples of the principles described herein and are part of the specification. The illustrated examples are given merely for illustration, and do not limit the scope of the claims.

Figure 1:
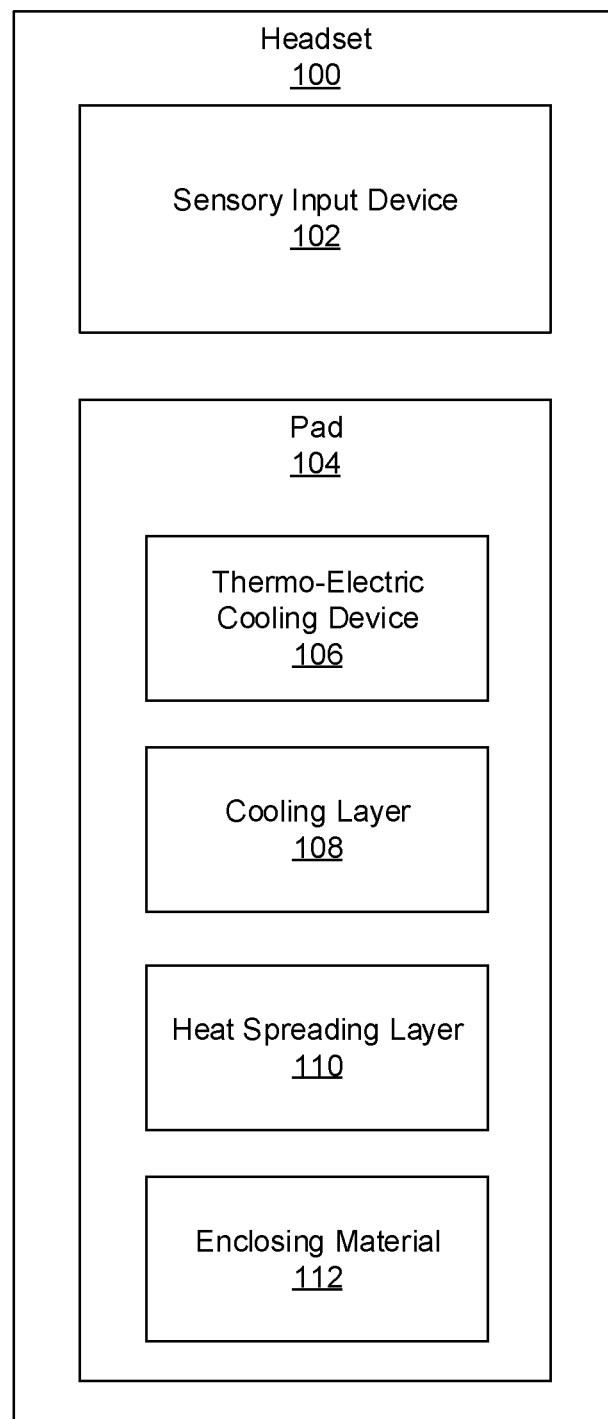
FIG. 1 is a block diagram of a thermo-electric cooling headset, according to an example of the principles described herein.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION

As described above, over the course of a day, many users adorn a headset to provide sensory input. For example, a user may use an audio headset with a microphone to engage in business or other phone calls with remote users. Audio headsets with or without microphones may be used for diversion as well. For example, video games provide audio feedback to a user and in some cases respond to audio commands. Accordingly, in these examples, audio headsets with or without microphones may be used to engage with these video games. Music, or other audio may similarly be streamed through a user-worn audio headset.

Video headsets also provide utility to a user by, for example providing a visual display that a user may view, and in some cases interact with, a visual environment. Such video headsets can generate realistic images, sounds, and other human discernable sensations that simulate a user's physical presence in a virtual environment presented at the headset.

Such enhanced reality systems and audio headsets provide countless hours of diversion and also provide new forms of digital interaction. However, developments may provide for an even more enjoyable experience for a user.

For example, headsets, often include a padded cushion coupled to the headset sensory input device (i.e., video display and/or speaker) which forms an enclosed volume around the sensory input organ (i.e., the ears or the eyes). The enclosed volume directs a sensory input to a wearer and restricts ambient interference for comfort as well as to suppress ambient noise from reaching the user's eyes and ears. The padded enclosed volume often acts as an insulator, capturing body heat released from the user's head. The captured heat may become uncomfortable during prolonged usage.

Accordingly, the present specification describes a headset and method for removing heat from a headset. In an example, doing so may enhance the comfort to the user. For example, the present headset and method reduce a heat build-up within a space that surrounds a sensory organ. This heat build-up can lead to discomfort, especially when headsets are worn for long periods of time, such as listening to music over the course of a day and/or extended gaming sessions. The present headset and method may enhance the effectiveness of pad cooling by using conductive fabric, cooling gel, a thermo-electric cooling (TEC) device, a heat spreading material, and a heat sink, for example.

Specifically, the present specification describes a headset. The headset includes a sensory input device and a pad surrounding the sensory input device. The pad includes a thermo-electric cooling (TEC) device having a first side and a second side. The first side is to cool and the second side is to heat when a voltage is applied to the TEC device. The pad also includes a cooling layer in contact with the first side of the TEC device and a heat spreading layer in contact with the second side of the TEC device. The pad also includes an enclosing material enveloping the pad.

The present specification also describes an audio headset. The audio headset includes a speaker to provide audio signals and a pad surrounding the speaker. The pad includes a thermo-electric cooling (TEC) device having a first side and a second side, the first side to cool and the second side to heat when a first voltage is applied to the TEC device. In this example, the TEC device includes an array of TEC elements formed on a flexible matrix. The pad also includes a cooling gel layer that is proximate a contact surface and in contact with the first side of the TEC device. The pad also includes a heat spreading layer that includes a first side in contact with the second side of the TEC device and a second side in contact with a heat sink. The pad also includes an enclosing material enveloping the pad.

In another example, the audio headset includes a pair of speakers to provide audio signals and a housing per speaker to retain the speaker. The audio headset also includes a torus-shaped pad surrounding each speaker. Each pad includes a heat sink coupled to, and disposed on top of the housing, a heat spreading layer disposed on top of the heat sink, a thermo-electric cooling (TEC) device disposed on top of the heat spreading layer, and a cooling layer disposed on top of the TEC device. In this example, the TEC device is to cool the cooling layer and is to transmit heat towards the heat spreading layer. Each pad also includes an enclosing material surrounding the heat sink, heat spreading layer, TEC device, and cooling layer.

The present specification also describes a method. According to the method, a temperature reading is received from a sensor disposed in an enclosed volume formed around a sensory input device. A difference between the temperature reading and a predetermined temperature is determined and, based on the difference, a TEC device that is disposed in the enclosed volume is activated to draw heat away from the enclosed volume.

Such systems and methods 1) allow for cooling of a sensory organ; 2) provides active cooling; and 3) monitors temperatures to ensure a desirable temperature range is maintained, as examples.

As used in the present specification and in the appended claims, the term, "controller" refers to various hardware components, which includes a processor and memory. The processor includes the hardware architecture to retrieve executable code from the memory and execute the executable code. As specific examples, the controller as described herein may include computer-readable storage medium, computer-readable storage medium and a processor, an application-specific integrated circuit (ASIC), a semiconductor-based microprocessor, a central processing unit (CPU), a field-programmable gate array (FPGA), a microcontroller, and/or other hardware device.

The memory may include a computer-readable storage medium, which computer-readable storage medium may contain, or store computer-usable program code for use by or in connection with an instruction execution system, apparatus, or device. The memory may take many types of memory including volatile and non-volatile memory. For example, the memory may include Random Access Memory (RAM), Read Only Memory (ROM), optical memory disks, flash memory, and magnetic disks, among others. The executable code may, when executed by the respective component, cause the component to implement at least the functionality described herein.

Figure 2:
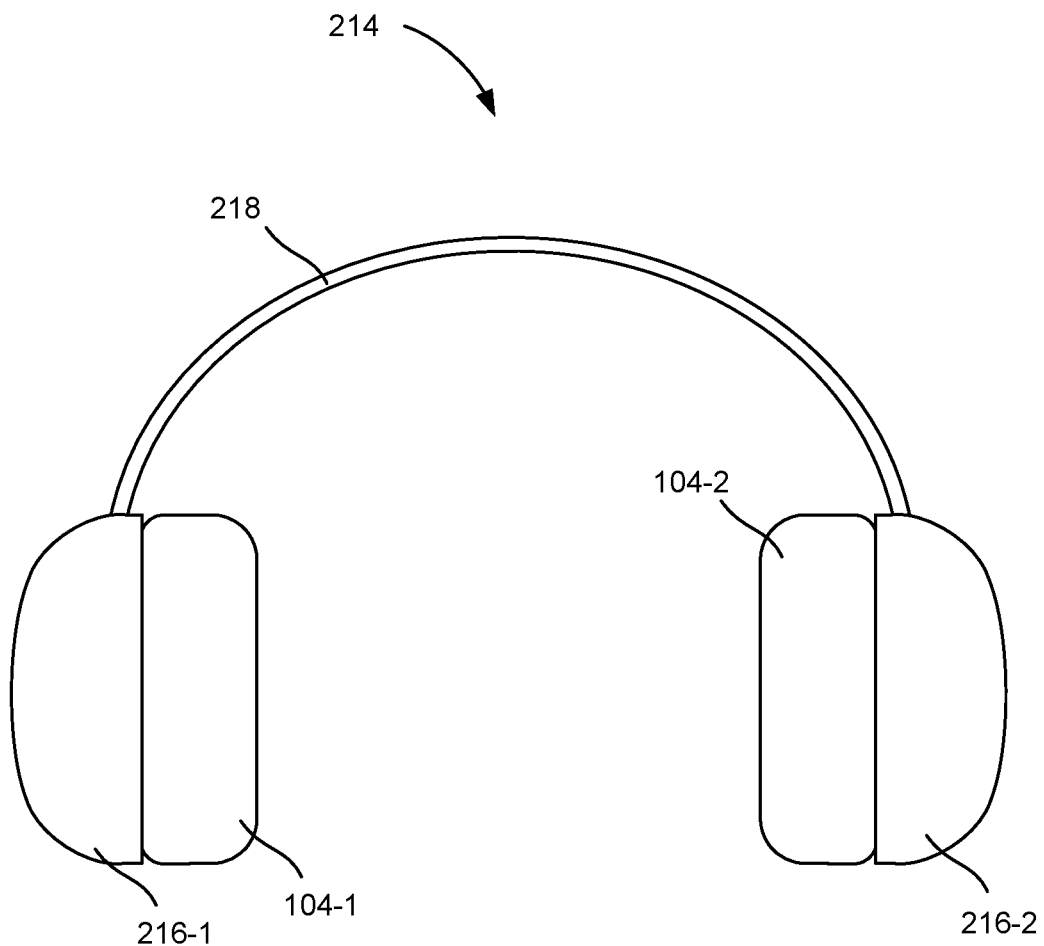
FIG. 2 is a diagram of a thermo-electric audio headset, according to an example of the principles described herein.
Figure 3:
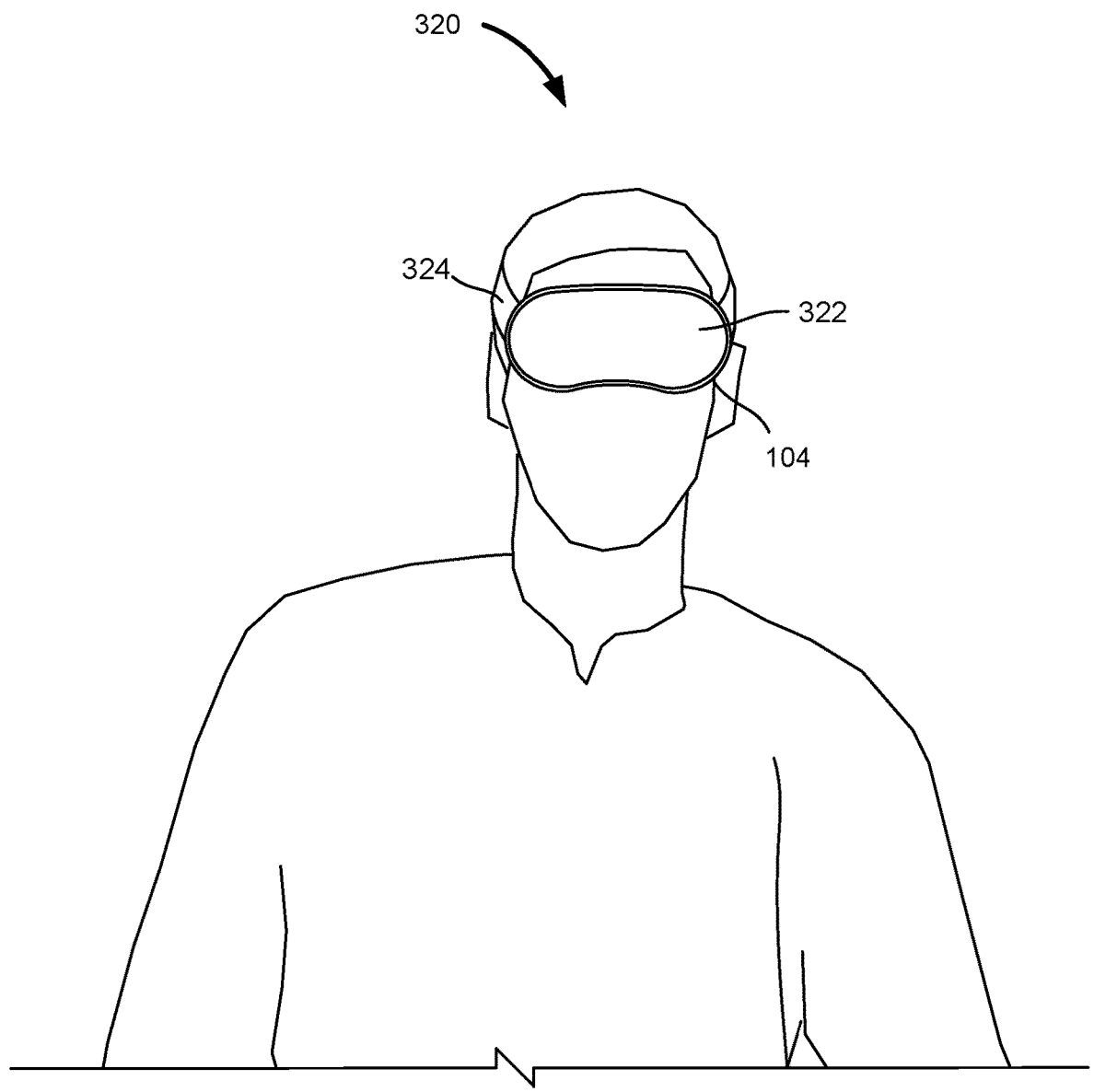
FIG. 3 is a diagram of a thermo-electric video headset, according to an example of the principles described herein.

Turning now to the figures, FIG. 1 is a block diagram of a thermo-electric cooling headset (100), according to an example of the principles described herein. As described above, the headset (100) may be used to provide a variety of sensory experiences to a user. Accordingly, the headset (100) may include a sensory input device (102) to provide the sensory experience. The sensory input device (102) may be of a variety of types. For example, the sensory input device (102) may be a speaker that outputs an audio signal. In this example, the headset (100) may be worn over the ears as depicted in FIG. 2. In another example, the sensory input device (102) may be a display screen that outputs a visual signal. In this example, the headset (100) may be worn over the eyes of the user as depicted in FIG. 3. In yet another example, the headset (100) may provide multiple sensory experiences. That is, the headset (100) may include both speakers and a display screen to provide an audio and visual experience.

The headset (100) may include a pad (104). In an example, the pad (104) surrounds the sensory input device (102) and provides an enclosed volume to more effectively direct the sensory stimulus to the user, while blocking out external stimuli which may interfere with the sensory experience. The pad (104) is also to provide comfort to the user. That is, the housing that contains the sensory input device (102) may be formed of a rigid material that would be uncomfortable when in contact with a user's skin. Accordingly, the pad (104) is a soft, deformable component that in an example 1) creates a comfortable contact point with the user's head and 2) blocks out external sensory signals to enhance the experience for the user.

As described above, due to heat emanating from a user and from heat generation by the sensory input device (102), the enclosed volume may heat up causing discomfort to the user. To combat this effect, the pad (104) includes a thermo-electric cooling (TEC) device (106) to move heat from within the enclosed volume. In general, a TEC device (106) utilizes the Peltier effect to transfer heat from one side of the TEC device (106) to the other. Specifically, a temperature difference is created between sides of the TEC device (106) when a voltage is applied to the two sides. In some examples, the TEC device (106) may include two different metal electrodes separated by a semiconductor material. As a voltage is applied to the electrodes, one side becomes cold and the other side becomes hot. In other words, when a voltage is applied, a first side of the TEC device (106) cools an adjacent surface while a second side of the TEC device (106) heats an adjacent surface. By reversing the polarity of the voltage, the first side of the TEC device (106) heats the adjacent surface while the second side of the TEC device (106) cools the adjacent surface. Accordingly, in one example, heat is transferred from within the enclosed volume around the sensory organ to an exterior of the enclosed volume via the TEC device (106), cooling layer (108), heat spreading layer (110), and enclosing material (112). By reversing the polarity of the applied voltage, the TEC device (106) and other components may transfer heat from outside the enclosed volume to inside the enclosed volume.

Accordingly, the pad (104) also includes a cooling layer (108) in contact with the first side of the TEC device (106) and a heat spreading layer (110) in contact with the second side of the TEC device (106). The cooling layer (108) may be adjacent a contact surface, i.e., the skin of the user, that is to be cooled, while the heat spreading layer (110) is on an opposite side and provides a path through which trapped heat is routed away from the user. Thus, the present pad (104), by using a TEC device (106) to cool a cooling layer (108) and transfer heat away towards the heat spreading layer (110), removes trapped heat away from the sensory organ. Accordingly, a user may experience more comfort as the headset (100) draws away any accumulating heat.

The pad (104) also includes an enclosing material (112) that envelopes the pad (104). This enclosing material (112) may maintain all the components of the pad (104) together and also provides additional comfort to the user. In some examples, the enclosing material may be a moisture-wicking and/or heat-wicking material to again draw heat away from a user wearing the headset (100).

FIG. 2 is a diagram of a thermo-electric audio headset (214), according to an example of the principles described herein. As illustrated in FIG. 2, the headset (FIG. 1, 100) may be an audio headset (214) in which the sensory input device (FIG. 1, 102) is an audio device, i.e. a speaker, to provide auditory stimulus to the user wearing the audio headset (214).

The headset (FIG. 1, 100) may provide the structure to support and hold the sensory input device (FIG. 1, 102) against a user. For example, as depicted in FIG. 2, the audio headset (214) may hold the speaker around a user's ear. Accordingly, the speakers may be disposed within housings (216). That is, a first housing (216-1) contains a right speaker and associated hardware while a second housing (216-2) contains a left speaker and associated hardware. The housings (216) are held over the ears via a headband (218) that rests on a user's head while wearing the audio headset (214).

The pad (104) may be shaped appropriately for the sensory organs targeted, i.e., the ears. For example, an audio headset (214) may include a first pad (104-1) for a right ear and a second pad (104-2) for a left ear. Accordingly, the enclosed volume in which the sensory input device (FIG. 1, 102) is disposed may provide a "cup" surrounding the sensory organ and may conform to a contact surface, i.e., a user's skin such that sensory input, such as audio and video, is directed to the respective sensory organ. Additionally, as described above, this cup restricts ambient sensory input, such as room noise, from interfering with the directed sensory input.

FIG. 3 is a diagram of a thermo-electric video headset (320), according to an example of the principles described herein. As illustrated in FIG. 3, the headset (FIG. 1, 100) may be a video headset (320) in which the sensory input device (FIG. 1, 102) is a visual display, i.e. a screen, to provide visual stimulus to the user wearing the video headset (320).

Enhanced reality systems allow a user to become immersed in an enhanced reality environment wherein they may be able to view, and in some cases interact with, a visual environment. For example, a head-mounted display, using stereoscopic display devices, allows a user to see, and become immersed in, any desired virtual scene. Such enhanced reality applications can provide visual stimuli, auditory stimuli, and/or can track user movement to create a rich immersive experience.

Enhanced reality systems allow a user to become immersed in an enhanced reality environment wherein they can interact with the enhanced environment. Enhanced reality systems include virtual reality (VR) systems, augmented reality (AR) systems, and mixed reality (MR) systems. Such enhanced reality systems can include enhanced reality headsets to generate realistic images, sounds, and other human discernable sensations that simulate a user's physical presence in a virtual environment presented at the headset. A VR system includes physical spaces and/or multi-projected environments. AR systems may include those systems and devices that implement live direct and/or indirect displays of a physical, real-world environment whose elements are augmented by computer-generated sensory input such as sound, video, graphics and/or GPS data. MR systems merge real and virtual worlds to produce new environments and visualizations where physical and digital objects co-exist and interact in real time. For simplicity, VR systems, AR systems, and MR systems are referred to herein as enhanced reality systems.

Accordingly, the video headset (320) may be a head-mounted display when utilized for virtual, augmented, and mixed reality implementations. A visual interface generates the visual display portion of the virtual reality. In some examples, the visual interface comprises virtual reality goggles that are worn by the user. These virtual reality goggles may include stereoscopic displays that add dimension to the displayed reality. The virtual reality device may also include an audio interface that provides a soundscape for the virtual reality environment that is created.

As with the audio headset (FIG. 2, 214), the video headset (320) may provide the structure to support and hold the sensory input device (FIG. 1, 102) against a user. For example, as depicted in FIG. 3, the video headset (320) may hold the visual interface around a user's eyes. Accordingly, the visual interface may be disposed within a housing (322). The housing (322) is held over the eyes via a strap (324). In one particular example, the headset (FIG. 1, 100) may hold multiple sensory input devices (FIG. 1, 102) against a user's eyes and ears for a fully immersive experience.

As in the audio headset (FIG. 2, 214), the pad (104) may be shaped appropriately for the sensory organs targeted, i.e., the eyes. For example, a video headset (320) may include a pad (104) that rests against a user's face. Accordingly, the enclosed volume in which the sensory input device (FIG. 1, 102) is disposed may provide a "cup" surrounding the sensory organ and may conform to a contact surface, i.e., a user's skin such that sensory input, such as audio and video, is directed to the respective sensory organ. Additionally, as described above, in some examples such a cup restricts ambient sensory input, such as room noise and lighting, from interfering with the directed sensory input.

Figure 4:
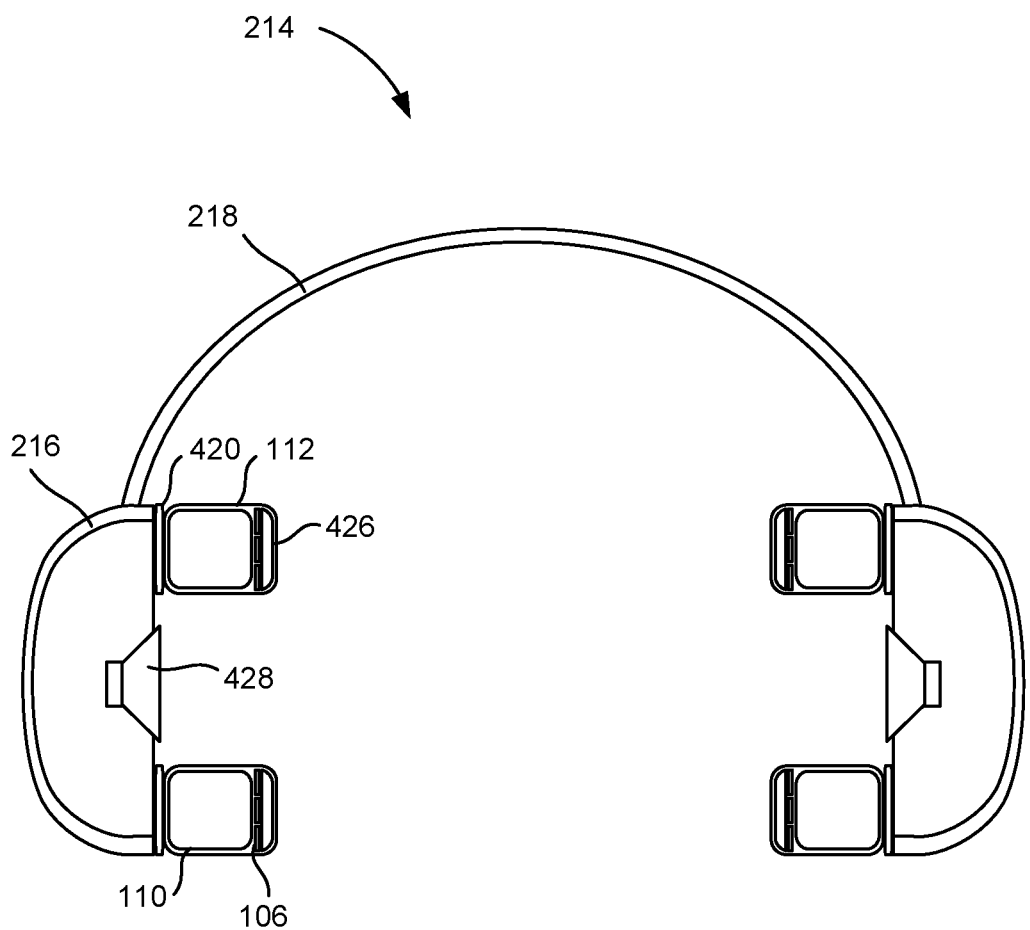
FIG. 4 is a cross-sectional diagram of a thermo-electric audio headset, according to an example of the principles described herein.

FIG. 4 is a cross-sectional diagram of a thermo-electric audio headset (214), according to an example of the principles described herein. While FIG. 4 depicts a cross-section of a pad (FIG. 1, 104) of an audio headset (214), the same cross-section applies to a pad (FIG. 1, 104) of other headsets (FIG. 1, 100), such as a video headset (320). For simplicity in FIG. 4, a single instance of different components are indicated with a reference number.

As depicted in FIG. 4, the cooling layer (FIG. 1, 108) is proximate a contact surface, that is a portion of the user's head surrounding the ear. The cooling layer (FIG. 1, 108) is in contact with the first side of the TEC device (106). As described above, this first side of the TEC device (106) is cooled when a voltage is applied to the TEC device (106). Such a cooling makes the cooling layer (FIG. 1, 108) colder than the environment in the enclosed volume surrounding the ear, such that any generated heat is pulled away from the enclosed volume by the cooling layer (FIG. 1, 108).

In some examples, the cooling layer (FIG. 1, 108) may be a cooling gel layer (426) which takes on the characteristic of the environment and maintains that temperature for a time being. As the cooling gel layer (426), which may be a silicone gel, is adjacent the TEC device (106) cool side, it is cooled. As described above, this draws heat away from the immediately adjacent contact area, i.e., the enclosed volume around an ear.

In this example, the heat spreading layer (110) is spaced apart from the contact surface by the TEC device (106) and is in contact with the second side of the TEC device (106). Accordingly, as the TEC device (106) is activated with a voltage, the first side is cooled and the second side is heated. As heat tends from a hotter location to a cooler location, the trapped heat from the enclosed volume around the ear is drawn away by the TEC device (106) cool side, after which it is ultimately drawn through the heat spreading layer (110) to be removed to a heat sink (420), which heat sink (420) is in contact with a second side of the heat spreading layer (110). The heat sink (420) may be a metal or air plate. Additional detail regarding the thermal dynamics of the heat transfer away from the enclosed volume is provided below in connection with FIG. 6.

FIG. 4 also depicts the speaker (428) of the audio headset (214) which provides the audio signals as well as the enclosing material (112) that envelopes the pad (FIG. 1, 104) components.

Figure 5:
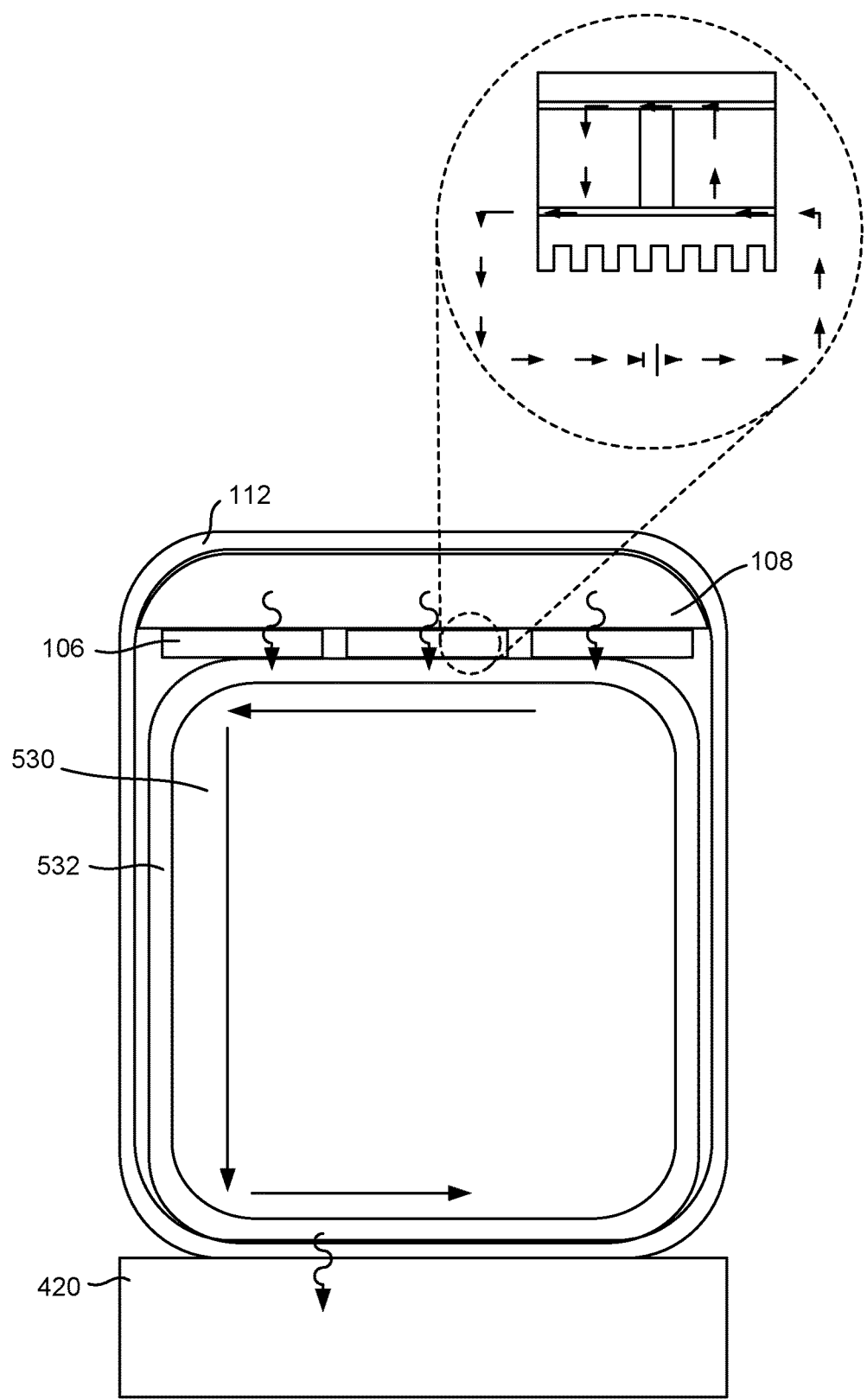
FIG. 5 is a cross-sectional view of the pad of a thermo-electric headset, according to an example of the principles described herein.

FIG. 5 is a cross-sectional view of the pad (104) of a thermo-electric headset (FIG. 1, 100), according to an example of the principles described herein. FIG. 5 clearly depicts the different layers of the pad (104), specifically the cooling layer (108), TEC device (106), heat spreading layer (FIG. 1, 110), enclosing material (112), and the heat sink (420). Specifically, FIG. 5 depicts an example of the pad (104), where each pad (104) includes a heat sink (420) coupled to, and disposed on top of the housing (FIG. 2, 216), a heat spreading layer (FIG. 1, 110) disposed on top of the heat sink (420), a thermo-electric cooling (TEC) device (106) disposed on top of the heat spreading layer (FIG. 1, 110), and a cooling layer (108) disposed on top of the TEC device (108). Each pad (104) also includes an enclosing material (112) surrounding the heat spreading layer (FIG. 1, 110), TEC device (106), and cooling layer (108).

Specifically, as described above, the cooling layer (108) may be a gel-like material that retains the temperature of whatever material surrounds, or is in contact with, the gel. In an example, this gel enhances heat conduction and comfort and absorbs heat from the skin and into the cool side of the TEC device (106). In other words, the cooling layer (108) may be formed of a gel, or any other material that retains a temperature of whatever environment it is in. In this example, the cooling layer (108) conforms to the temperature of a TEC device (106) with which it has contact.

Accordingly, the cooling layer (108), which may be close to a contact surface such as a user's ear, may draw heat away from the contact surface. Specifically, the first side of the TEC device (106), when a voltage is applied to the TEC device (106), cools the cooling layer (108), which draws heat away from an enclosed volume that surrounds a person's sensory organ.

As depicted in FIG. 5, the TEC layer (106) is formed of multiple layers. A first ceramic sheet is in contact with the cooling layer (108), which ceramic sheet is in contact with an etched conductor to create series and parallel conduction paths. Dissimilar metal towers are created from conductors, such as Bismuth telluride. Another etched conductor sheet is at the bottom of the towers, which second etched conductor sheet is in contact with another ceramic sheet in contact with the heat spreading layer (FIG. 1, 110).

As described above, a voltage is applied by a voltage source resulting in electron flow as indicated in FIG. 5 which absorbs heat from the cooling layer (108) and emits heat towards the heat spreading layer (FIG. 1, 110).

The second side of the TEC layer (106), due to the characteristics of a TEC device (106), is heated to a warmer temperature than the first side such that any heat energy drawn from the cooling layer (108) continues on to this second side, as depicted in FIG. 5.

Absorbed heat is then transferred to a heat spreading layer (FIG. 1, 110) as depicted by the curved lines between the cooling layer (108) and the TEC device (106). In some examples, the heat spreading layer (FIG. 1, 110) includes a core (530) wrapped with a thermally conductive fabric (532). That is, the core (530) and the thermally conductive fabric (532) form one example of a heat spreading layer (FIG. 1, 110). However, the heat spreading layer (FIG. 1, 110) may take a variety of forms. The core (530) may be made of a soft material, such as foam and provides a cushion against the contact surface, i.e., the user's skin.

The thermally conductive fabric (532) may be any material that provides in-plane thermal conduction. In other words, rather than the trapped heat being conducted through the core (530), heat is transferred along the thermally conductive fabric (532) towards the heat sink (420) as depicted by the straight arrows. That is, the thermally conductive fabric (532) defines a conduction path from a first side that is in contact with the TEC device (106) towards a second, and opposite side that is in contact with the heat sink (420). Specifically, the heat conductive fabric (532) may be a graphite fiber which has excellent thermal properties. In another example, the heat conductive fabric (532) may be graphene.

By placing the TEC device (106) in close proximity to the skin, a much larger change in temperature is found between the enclosed volume and the TEC device (106), which allows for an increased heat transfer away from the contact surface. As described above, waste heat is then dissipated over the long thermally conductive fabric (532) runs. In this example, this configuration utilizes the length of the thermally conductive fabric (532) run to enhance the heat dissipation, enhancing the cooling process. In some examples, in addition to conduction of heat away from the contact surface via the heat spreading layer (FIG. 1, 110), heat is also released via convection to the environment as it travels along the conduction path.

In other words, as shown in FIG. 5, the wrapping of the thermally conductive fabric (532) around the core (530) creates a heat spreading layer (FIG. 1, 110) which moves thermal energy. In a passive implementation, the heat spreading layer (FIG. 1, 110) may move thermal energy from the enclosed volume around the sensory organ to the heat sink (420). In an active cooling implementation, the thermally conductive properties of the heat spreading layer (FIG. 1, 110) accelerate the movement of thermal energy from the TEC device (106).

In some examples, the thermally conductive fabric (532) may be constructed of a graphite sheet. The thermally conductive fabric (532) may be lightweight, flexible and have high thermally conductive properties. The thermally conductive fabric (532) may include heat spreading capabilities. The thermally conductive fabric (532) may be cut to provide full three-dimensional coverage of the pad (104).

As shown in FIG. 5, the entire assembly, in one example, is enclosed in a comfortable enclosing material (112) which may also enhance heat conduction. Such an enclosing material (112) may be thermally conductive, heat-wicking, and sweat-wicking to aid in heat conduction and that is also comfortable to a user.

Figure 6:
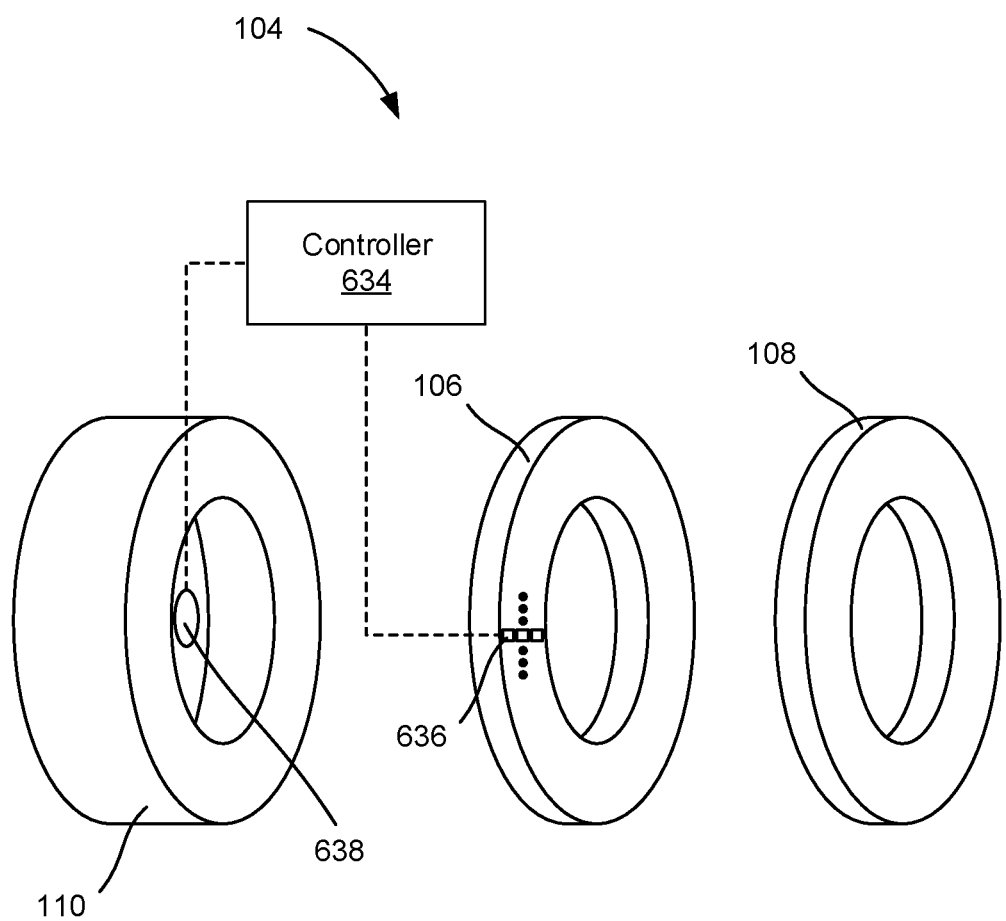
FIG. 6 is an exploded view of the pad of a thermo-electric audio headset, according to an example of the principles described herein.

FIG. 6 is an exploded view of the pad (104) of a thermo-electric audio headset (FIG. 2, 214), according to an example of the principles described herein. As clearly depicted in FIG. 6, the pad (104) is shaped to form an enclosed volume around the sensory organ. In the case of an audio headset (FIG. 2, 214), the pad (104) may be torus-shaped to surround the ear.

FIG. 6 also provides additional details regarding the TEC device (106). Specifically, in some examples, the TEC device (106) includes an array of TEC elements (636) coupled to a flexible matrix material. That is, as described above, a TEC element (636) may be formed of two metal and rigid plates. In some examples, each TEC element (636) is four millimeters by four millimeters.

By placing TEC elements (636) on a flexible matrix material, the TEC device (106) can conform to the contact surface regardless of the rigidity of the individual TEC elements (636). For simplicity, three TEC elements (636) are depicted in FIG. 6; however, the entire ring of the matrix material may be covered with TEC elements (636). Each TEC element (636) may be electrically coupled to the controller (634), such that each may be activated to draw heat away from the enclosed volume.

In some examples, the headset (FIG. 1, 100) includes additional components. For example, the headset (FIG. 1, 100) may include 1) a sensor (638) to measure a temperature of the enclosed volume formed by the pad (104) and 2) a controller (634). In this example, the controller (634) receives a temperature reading from the sensor (638), determines a difference between the temperature reading and a predetermined value, and activates the TEC device (106) based on the difference. That is, the sensor (638) provides for a closed loop feedback as to when and when not to activate the TEC elements (636). Accordingly, the controller (634) may include in memory a predetermined temperature against which the temperature reading is compared.

In other words, the sensor (638) which communicatively connected to the controller (634) may provide control for the TEC device (106). In some examples, the sensor (638) may be mounted within the pad (104), or to another part of the structure that forms the "cup" around the sensory organ.

The sensor (638) may be any sensor (638) that can be utilized for measuring temperatures of the enclosed volume. Examples include thermistors, thermocouples, resistance thermometers, and silicon bandgap temperature sensors.

The controller (634) may be communicatively coupled to the sensor (638) and the TEC device (106). The controller (634) may provide the computational functionality to receive a temperature reading from the sensor (638), compare the temperature reading to a predetermined temperature, and calculate a difference between the temperature reading and the predetermined temperature. The controller (634) may factor constants or functional changes to the difference based on identified temperature differences between the sensor (638) and the enclosed volume.

In addition to activating the TEC device (106), the controller (634) may deactivate the TEC device (106) once the temperature reading has returned to within a threshold range of the predetermined temperature.

As noted above, in addition to drawing heat away from the enclosed volume, i.e., cooling the ear, the system may transfer heat to the enclosed volume, i.e., heating the ear. Accordingly, in some examples, the controller (634) may reverse the polarity of the applied voltage supplied to the TEC device (106). By the reversal of the polarity of the applied voltage, the TEC device (106) may transfer heat into the enclosed volume.

The controller (634) may receive instructions from an external system. The instructions may correspond to providing the predetermined temperature as well as the threshold. The predetermined temperature and the threshold may be a part of a user profile which may be crafted by the user to meet their specific criteria. In other examples, the predetermined temperature and threshold may be a part of an application package designed to provide temperature control for an immersive experience. Examples of application packages providing immersive experiences may include video games, virtual or mixed reality applications, and video players. In other words, the controller (634) may take as user input, either via buttons, or via program code running on the system the headset is connected to, which user input sets and/or controls temperature settings.

Figure 7:
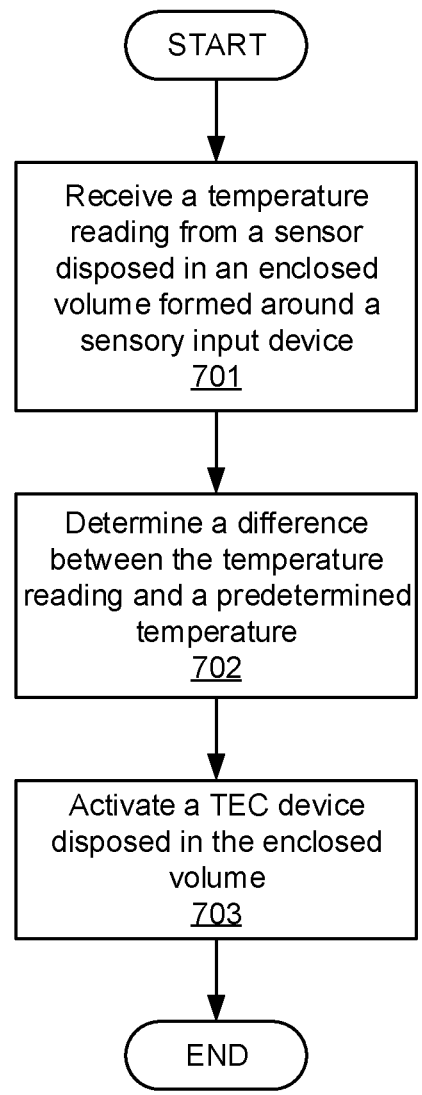
FIG. 7 is a flow chart of a method for controlling a thermo-electric cooling device of a thermo-electric headset, according to an example of the principles described herein.

FIG. 7 is a flow chart of a method (700) for controlling a thermo-electric cooling device (FIG. 1, 106) of a thermo-electric headset (FIG. 1, 100), according to an example of the principles described herein. According to the method (700), a controller (FIG. 6, 634) receives (block 701) a temperature reading from a sensor (FIG. 6, 638) disposed in an enclosed volume around a sensory input device (FIG. 1, 102). The controller (FIG. 6, 634) may request or directly access the sensor (FIG. 6, 638) for a temperature reading.

The controller (FIG. 6, 634) determines (block 702) a difference between the temperature reading and a predetermined temperature, which predetermined temperature may be a maximum comfort level temperature for a user.

The controller (FIG. 6, 634) activates (block 703) a TEC device (FIG. 1, 106) based on the difference. This may be done by applying voltage directly to the TEC device (FIG. 1, 106), or by signaling a subsystem of the TEC device (FIG. 1, 106) to activate the TEC device (FIG. 1, 106). In so doing, heat is drawn away from the enclosed volume by transferring heat in-plane away from the enclosed volume through a thermally conductive material.

Such systems and methods 1) allow for cooling of a sensory organ; 2) provides active cooling; and 3) monitors temperatures to ensure a desirable temperature range is maintained, as examples.

What is claimed is:

1. A headset, comprising:
  a sensory input device; and
  a pad surrounding the sensory input device, the pad comprising:
    a thermo-electric cooling (TEC) device having a first side and a second side, wherein the first side is to cool and the second side is to heat when a voltage is applied to the TEC device;
    a cooling layer in contact with the first side of the TEC device;
    a heat spreading layer in contact with the second side of the TEC device; and
    an enclosing material enveloping the pad.

2. The headset of claim 1, wherein:
  the cooling layer is to be proximate a contact surface; and
  the heat spreading layer is spaced apart from the contact surface by the TEC device.

3. The headset of claim 1, wherein:
  the heat spreading layer comprises a core wrapped with a thermally conductive fabric; and
  the thermally conductive fabric defines a conduction path from a first side of the heat spreading layer in contact with the TEC device to a second, and opposite, side of the heat spreading layer.

4. The headset of claim 3, further comprising a heat sink coupled to the second side of the heat spreading layer.

5. The headset of claim 1, wherein the pad conforms to a contact surface.

6. The headset of claim 1, wherein the sensory input device is a visual display.

7. The headset of claim 1, wherein the sensory input device is an audio device.

8. The headset of claim 1, wherein the cooling layer comprise a silicone gel.

9. The headset of claim 1, wherein the TEC device comprises an array of TEC elements coupled to a flexible matrix material.

10. The headset of claim 1, wherein the enclosing material is a heat-wicking material.

11. An audio headset, comprising:
  a speaker to provide audio signals; and
  a pad surrounding the speaker, the pad comprising:
    a thermo-electric cooling (TEC) device having a first side and a second side, wherein the first side is to cool and the second side is to heat when a voltage is applied to the TEC device, wherein the TEC device comprises an array of TEC elements formed on a flexible matrix;
    a cooling gel layer:
      proximate a contact surface; and
      in contact with the first side of the TEC device;
    a heat spreading layer comprising:
      a first side in contact with the second side of the TEC device; and
      a second side in contact with a heat sink; and
    an enclosing material enveloping the pad.

12. The audio headset of claim 11, wherein the pad is torus-shaped.

13. The audio headset of claim 11, further comprising:
a sensor to measure a temperature of an enclosed volume formed by the pad; and
a controller to:
  receive a temperature reading from the sensor;
  determine a difference between the temperature reading and a predetermined temperature; and
  activate the TEC device based on a determined difference.

14. An audio headset, comprising:
a pair of speakers to provide audio signals;
a housing per speaker to retain the speaker;
a torus-shaped pad surrounding each speaker, the pad comprising:
  a heat sink coupled to, and disposed on top of the housing;
  a heat spreading layer disposed on top of the heat sink;
  a thermo-electric cooling (TEC) device disposed on top of the heat spreading layer;
  a cooling layer disposed on top of the TEC device, wherein the TEC device is to cool the cooling layer and is to transmit heat towards the heat spreading layer; and
  an enclosing material surrounding the heat sink, heat spreading layer, TEC device, and cooling layer.

15. The audio headset of claim 14, wherein the heat spreading layer comprises:
a padded core; and
a heat spreading fabric wrapped around the padded core.

16. The audio headset of claim 14, further comprising a controller to activate the TEC device.

17. The audio headset of claim 16, wherein the controller is to activate the TEC device based on a user input.

18. The audio headset of claim 11, wherein the heat spreading layer comprises a core wrapped with a thermally conductive fabric.

19. The audio headset of claim 18, wherein the core comprises foam material.

20. The audio headset of claim 19, wherein the thermally conductive fabric defines a conduction path around the core from the first side of the heat spreading layer in contact with the TEC device to the second side of the heat spreading layer in contact with the heat sink.

* * * * *